(12) United States Patent
Chang et al.

(10) Patent No.: US 11,123,213 B2
(45) Date of Patent: Sep. 21, 2021

(54) LIFTING BELT

(71) Applicants: Ki Yong Chang, Seoul (KR); Min Young Kang, Seoul (KR)

(72) Inventors: Ki Yong Chang, Seoul (KR); Min Young Kang, Seoul (KR)

(*) Notice: Subject to any disclaimer, the term of this patent is extended or adjusted under 35 U.S.C. 154(b) by 307 days.

(21) Appl. No.: 15/777,913

(22) PCT Filed: Dec. 1, 2016

(86) PCT No.: PCT/KR2016/014029
§ 371 (c)(1),
(2) Date: May 22, 2018

(87) PCT Pub. No.: WO2018/016692
PCT Pub. Date: Jan. 25, 2018

(65) Prior Publication Data
US 2018/0338853 A1  Nov. 29, 2018

(30) Foreign Application Priority Data

Jul. 22, 2016  (KR) .................. 10-2016-0093198
Oct. 18, 2016  (KR) .................. 10-2016-0135230

(51) Int. Cl.
*A61F 5/03* (2006.01)
*A61F 5/02* (2006.01)
*A61F 5/34* (2006.01)

(52) U.S. Cl.
CPC .............. *A61F 5/028* (2013.01); *A61F 5/024* (2013.01); *A61F 5/34* (2013.01)

(58) Field of Classification Search
CPC .......... A61F 5/024; A61F 5/026; A61F 5/028; A61F 5/34; A61F 5/0009; A61F 5/012; A61F 5/05816; A63B 21/4009; A63B 21/4001; A63B 21/065; A41F 9/007; A41F 9/025; A41F 9/02
USPC ...................................... 602/13, 19
See application file for complete search history.

(56) References Cited

U.S. PATENT DOCUMENTS

| | | | | |
|---|---|---|---|---|
| 4,135,503 A | * | 1/1979 | Romano | A61F 5/028 128/118.1 |
| 4,682,587 A | | 7/1987 | Curlee | |
| 4,682,588 A | * | 7/1987 | Curlee | A61F 5/028 128/DIG. 20 |
| 4,703,750 A | * | 11/1987 | Sebastian | A61F 5/34 602/13 |

(Continued)

FOREIGN PATENT DOCUMENTS

| CN | 103126855 | 6/2013 |
|---|---|---|
| CN | 104800045 | 7/2015 |

(Continued)

OTHER PUBLICATIONS

"International Search Report (Form PCT/ISA/210) of PCT/KR2016/014029", dated Apr. 21, 2017, pp. 1-3.

(Continued)

*Primary Examiner* — Camtu T Nguyen
(74) *Attorney, Agent, or Firm* — JCIPRNET

(57) ABSTRACT

A lifting belt may include a lifter configured to generate a tractive force along a longitudinal direction of a spinal column by expansion, and a left connector and a right connector respectively disposed on a left side and a right side of the lifter and connectable to each other.

7 Claims, 7 Drawing Sheets

(56) References Cited

U.S. PATENT DOCUMENTS

| | | | | |
|---|---|---|---|---|
| RE34,883 E | * | 3/1995 | Grim | A61F 5/028 602/13 |
| 5,728,055 A | | 3/1998 | Sebastian | |
| 5,833,638 A | * | 11/1998 | Nelson | A61F 5/028 602/19 |
| 8,012,113 B2 | * | 9/2011 | Lee | A61F 5/028 128/96.1 |

FOREIGN PATENT DOCUMENTS

| | | |
|---|---|---|
| KR | 100142202 | 3/1998 |
| KR | 100997574 | 11/2010 |
| KR | 20130095935 | 8/2013 |

OTHER PUBLICATIONS

"Written Opinion of the International Searching Authority of PCT/KR2016/014029", dated Apr. 21, 2017, p. 1-p. 5.

\* cited by examiner

[Fig. 1a]
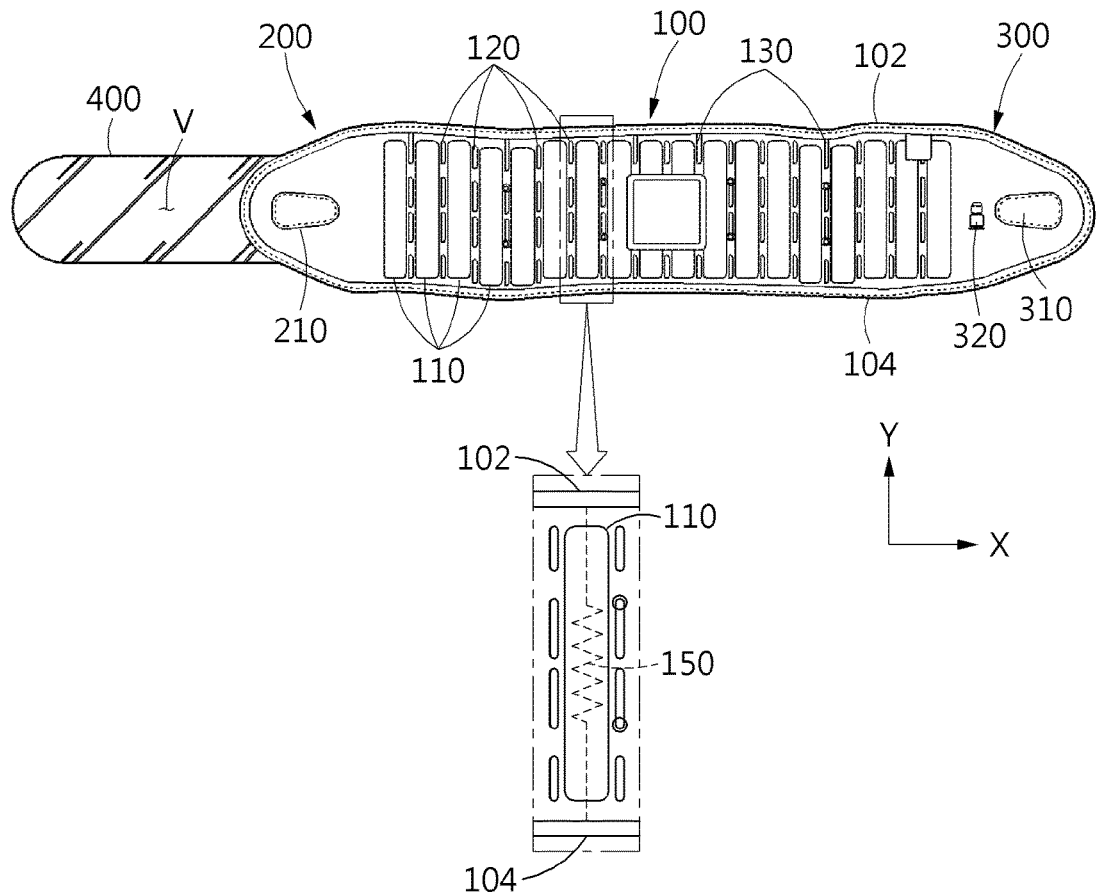
[Fig. 1b]
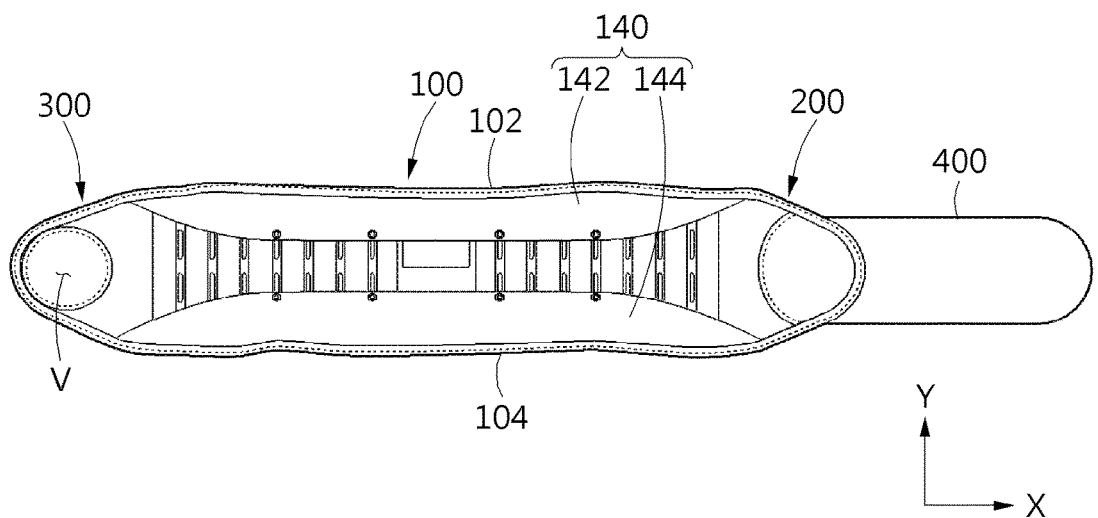

[Fig. 1c]
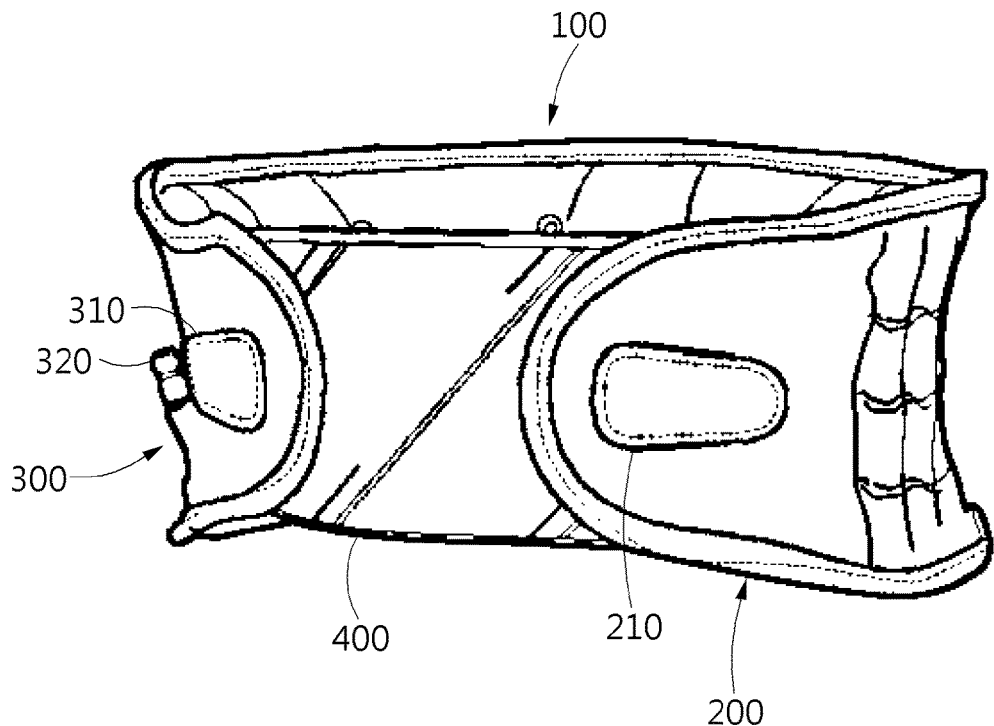
[Fig. 2a]
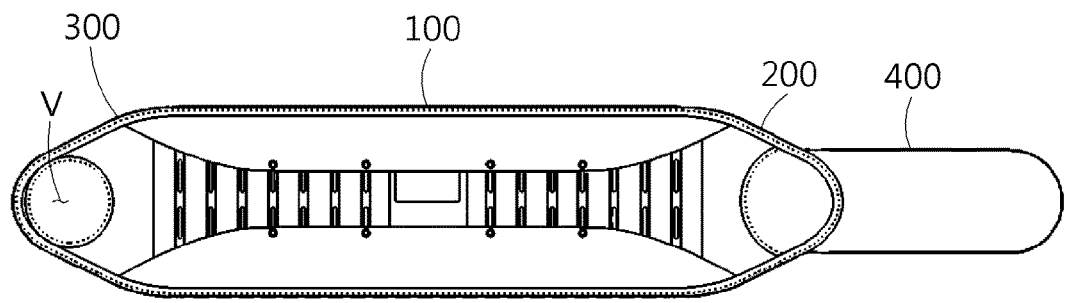
[Fig. 2b]
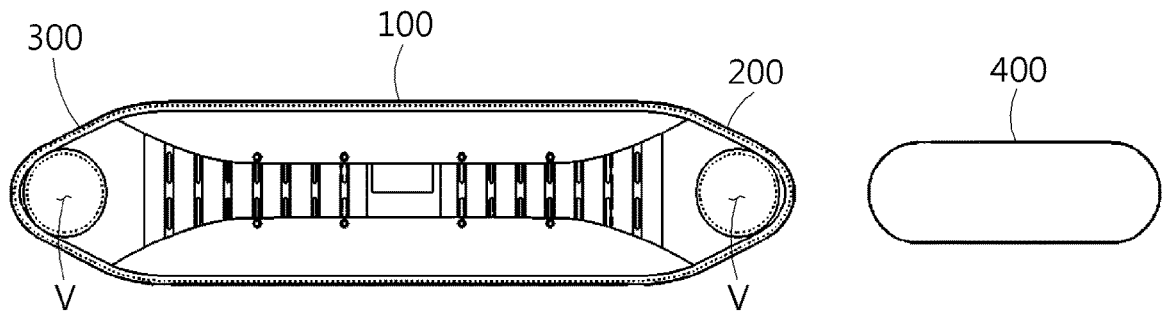

[Fig. 3]
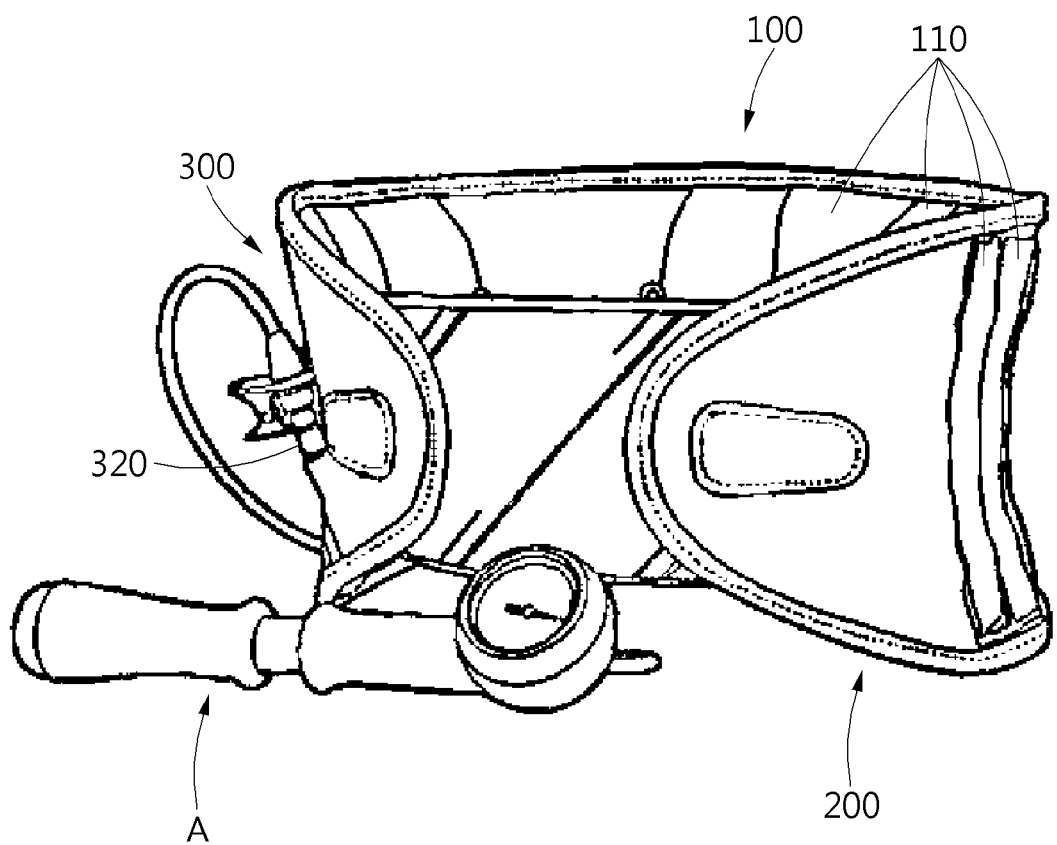

[Fig. 4a]
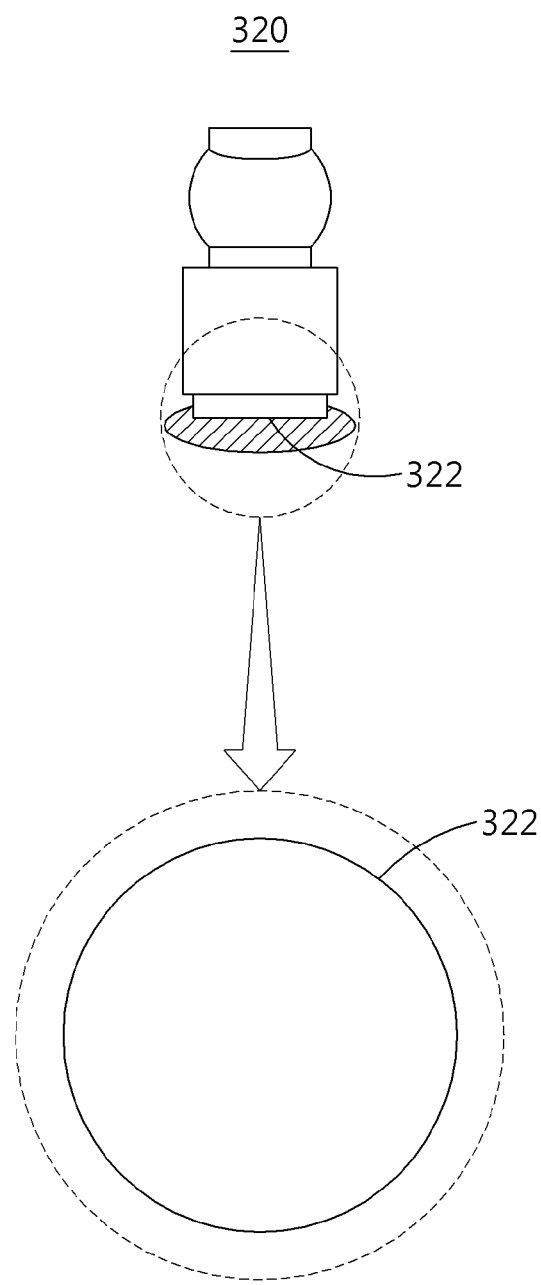

[Fig. 4b]
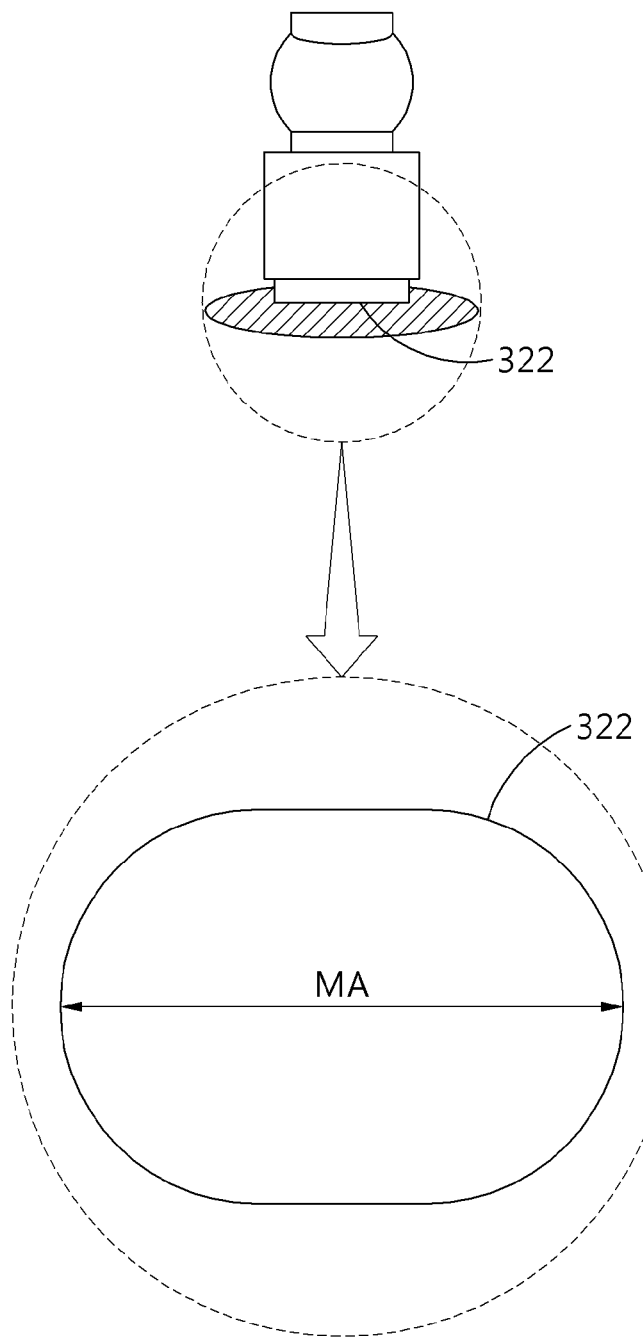

[Fig. 5a]
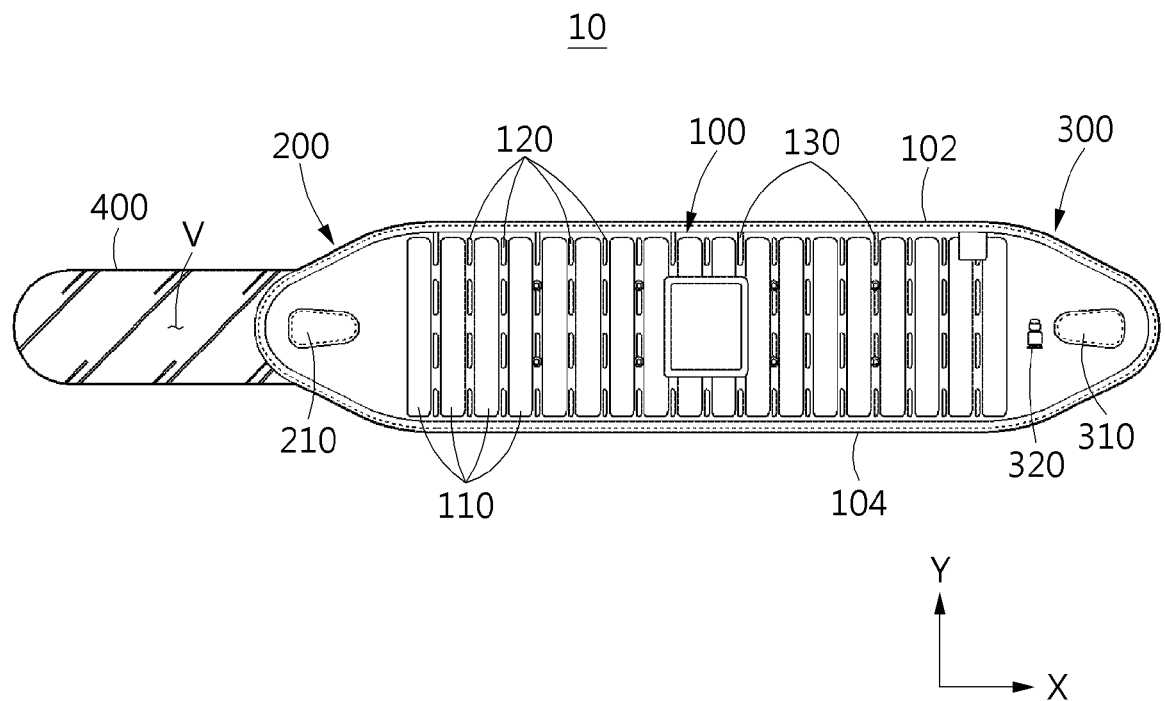
[Fig. 5b]
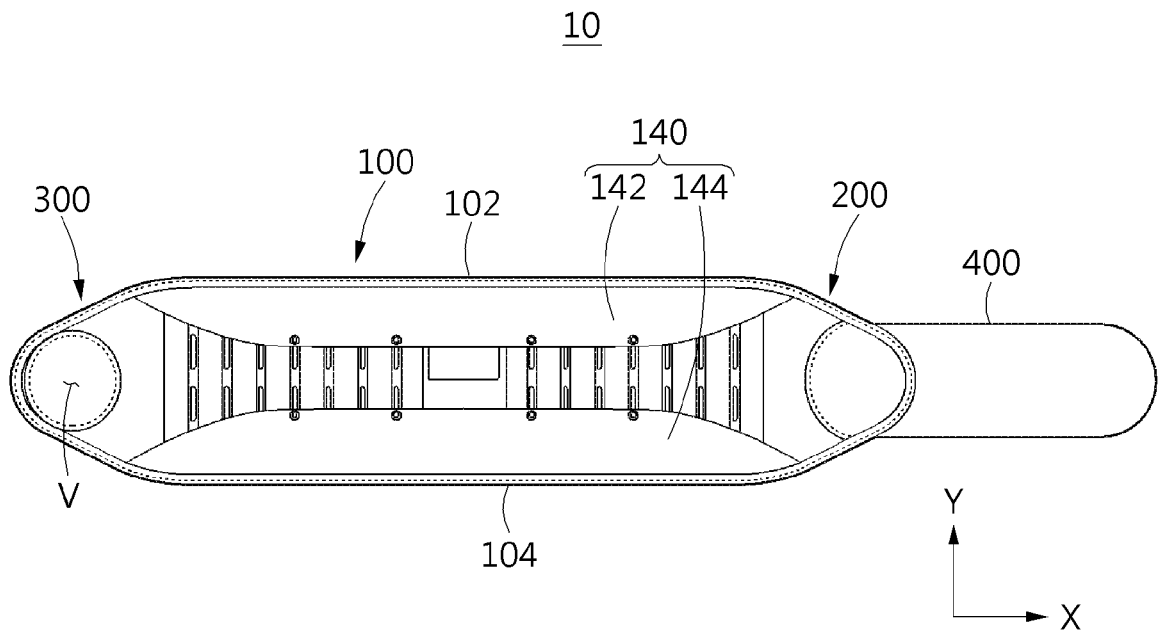

[Fig. 5c]
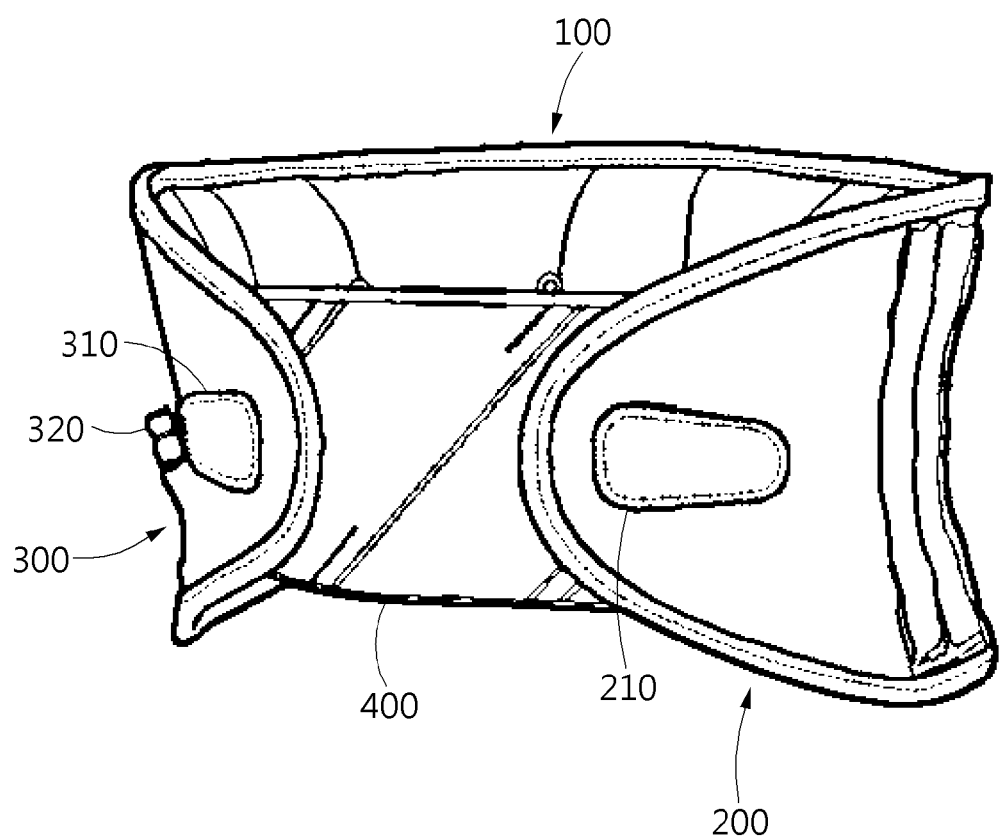

LIFTING BELT

TECHNICAL FIELD

The present disclosure relates to a lifting belt, and more particularly, to a lifting belt that may stably support muscles around a waist of a user by lifting a spinal column of the user upwards and downwards by injection of a fluid, and thereby being transformed to be elastic in response to a curve or a movement of the waist.

BACKGROUND ART

A generally-used waist lifting belt may aid a disc in recovering from a deformed state to be an original state by pulling a pelvis and a waist in opposite directions and lifting a space between vertebrae of a centrum not to receive a pressure of an upper body.

Most of generally-used waist lifting belts may use an air injection method, which uses a tube including a plurality of air passages in a vertical direction in a belt, and may inject air into a shrunk tube and allow the tube to be expanded and stretched in a vertical direction in order to lift or support a waist.

However, such a generally-used waist lifting belt may press an abdomen and also intestines, and may thus induce indigestion, poor blood circulation, and the like, because a volume of the tube increases in inner and outer direction, in addition to the vertical direction, while the shrunk tube is being expanded by the injection of air.

In addition, since all the air passages are connected to one another, a disc may deteriorate when any one portion of the air passages is pressed and an air pressure is concentrated in another portion. Further, a portion that is lifted when a waist moves may be contracted again, and thus a lifting effect may not be generated at the time.

Thus, various types of a lifting belt are under development.

For example, Korean Patent Application No. 10-2012-0017357 filed on Feb. 21, 2012, discloses a waist lifting belt including an articulated joint.

DISCLOSURE OF INVENTION

Technical Problem

An aspect of the present disclosure provides a lifting belt that may apply a fluid pressure or a tractive force only upwards and downwards, for example, in a vertical direction, to allow a spinal column of a user to resist gravity, and vertically lift a weight of an upper body of the user.

Another aspect of the present disclosure also provides a lifting belt that may stably and strongly lift a spinal column of a user, and also be elastically transformed in response to a curve or a movement of a waist of the user to stably support muscles around the waist.

Still another aspect of the present disclosure also provides a lifting belt that may prevent an edge of an upper end and a lower end of a lifter of the lifting belt from being spread towards an outer side by injection of a fluid, and relieve a pressure applied to an abdomen.

Yet another aspect of the present disclosure also provides a lifting belt that may suggest, to a user, a desirable position around which the lifting belt is to be worn, and thus allow the user to obtain more effects from the lifting belt in lifting a spinal column of the user and supporting muscles around a waist of the user.

Further another aspect of the present disclosure also provides a lifting belt that may be applicable to various users, for example, a lumber disc patient experiencing a surgery or recovering from the surgery, an acute or chronic strain patient, and a student preparing examination, a worker or an employee, and a driver who are sedentary for most of times and thus need to have correction of posture, and an athlete who needs rehabilitation, and may thus be used to protect or treat a disc.

Solution to Problem

According to an aspect of the present disclosure, there is provided a lifting belt including a lifter configured to generate a tractive force along a longitudinal direction of a spinal column by expansion, and a left connector and a right connector respectively disposed on a left side and a right side of the lifter and connectable to each other.

A length of an upper end of the lifter may be shorter than a length of a lower end of the lifter.

The lifter may include a plurality of expanding portions extended in the longitudinal direction of the spinal column and configured to be expanded by injection of a fluid.

The lifter may further include a plurality of cut portions disposed adjacent to the upper end of the lifter, among the expanding portions.

A cut width of each of the cut portions may increase towards the lower end of the lifter from the upper end of the lifter, and the cut width may be decreased by expansion of the expanding portions.

The lifter may further include a plurality of blocking portions disposed in a vertical direction of the lifter, among the expanding portions.

The lifter may include at least one flap member disposed in an inner surface of the lifter, and a total height of the at least one flap member may be shorter than a height of the lifter.

The lifter may include a plurality of flap members disposed in an inner surface of the lifter, and the flap members may include a first flap member extended to a center of the lifter from the upper end of the lifter and a second flap member extended to the center of the lifter from the lower end of the lifter.

The left connector or the right connector may include a fluid injection member configured to supply a fluid to the lifter. A lower end of the fluid injection member may be provided in an oval shape, and a major axis from the lower end of the fluid injection member may be parallel to the upper end or the lower end of the lifter.

The lifter may include an elastic member configured to connect the upper end of the lifter and the lower end of the lifter, and the elastic member may be deformed or return to an original state by a change in a form of the lifter.

The left connector and the right connector may be bilaterally symmetrical with each other from the lifter, and the lifting belt may further include a central connector attachable to or detachable from at least one of the left connector and the right connector.

The left connector and the right connector may include a plurality of indication members, and the indication members may include a first indication member disposed on an outer surface of the left connector and a second indication member disposed on an outer surface of the right connector. The central connector may be disposed between the first indication member and the second indication member.

Advantageous Effects of Invention

According to example embodiments, a lifting belt may apply a fluid pressure or a tractive force only upwards and downwards, for example, in a vertical direction, to allow a spinal column of a user to resist gravity, and vertically lift a weight of an upper body of the user.

According to example embodiments, a lifting belt may stably and strongly lift a spinal column of a user, and also be elastically deformed in response to a curve or a movement of a waist of the user to stably support muscles around the waist.

According to example embodiments, a lifting belt may prevent an edge of an upper end and a lower end of a lifter of the lifting belt from being spread towards an outer side by injection of a fluid, and relieve a pressure applied to an abdomen.

According to example embodiments, a lifting belt may suggest, to a user, a desirable position around which the lifting belt is to be worn, and thus allow the user to obtain more effects from the lifting belt in lifting a spinal column of the user and supporting muscles around a waist of the user.

According to example embodiments, a lifting belt may be applicable to various users, for example, a lumber disc patient experiencing a surgery or recovering from the surgery, an acute or chronic strain patient, and a student preparing examination, a worker or an employee, and a driver who are sedentary for most of times and thus need to have correction of posture, and an athlete who needs rehabilitation, and may be used to protect or treat a disc.

BRIEF DESCRIPTION OF DRAWINGS

FIGS. 1a through 1c illustrate a lifting belt into which a fluid is not injected according to an example embodiment.

FIGS. 2a and 2b illustrate an integral-type central connector and a separate-type central connector according to an example embodiment.

FIG. 3 illustrates connection between a fluid injection member of a lifting belt and a fluid injector according to an example embodiment.

FIGS. 4a and 4b illustrate a circular shape and an oval shape of a lower end of a fluid injection member of a lifting belt according to an example embodiment.

FIGS. 5a through 5c illustrate a lifting belt into which a fluid is injected according to an example embodiment.

MODE FOR THE INVENTION

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

Terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected," "coupled," or "joined" to another component, a third component may be "connected," "coupled," and "joined" between the first and second components, although the first component may be directly connected, coupled or joined to the second component.

FIGS. 1a through 1c illustrate a lifting belt into which a fluid is not injected according to an example embodiment. FIGS. 2a and 2b illustrate an integral-type central connector and a separate-type central connector according to an example embodiment. FIG. 3 illustrates connection between a fluid injection member of a lifting belt and a fluid injector according to an example embodiment. FIGS. 4a and 4b illustrate a circular shape and an oval shape of a lower end of a fluid injection member of a lifting belt according to an example embodiment. FIGS. 5a through 5c illustrate a lifting belt into which a fluid is injected according to an example embodiment.

Referring to FIGS. 1a through 1c, a lifting belt 10 according to an example embodiment includes a lifter 100, a left connector 200, a right connector 300, and a central connector 400.

FIG. 1a illustrates an outer side of the lifting belt 10, FIG. 1b illustrates an inner side of the lifting belt 10, and FIG. 1c illustrates the lifting belt 10 of which the right connector 300 and the central connector 400 are connected to each other.

The lifter 100 may be wrinkled overall before a fluid is injected, and an upper end 102 and a lower end 104 of the lifter 100 may be piped not to apply an unnecessary pressure to a user.

The lifter 100 may have a length extended in a lateral direction, or an x axis, along a torso of the user, and a height extended in a longitudinal direction, or a y axis, along a longitudinal direction of a spinal column of the user.

The lifter 100 includes a plurality of expanding portions 110, a plurality of blocking portions 120, and a plurality of cut portions 130.

The expanding portions 110 may be extended in the longitudinal direction of the spinal column, or extended upwards and downwards from the lifter 100, for example, in a vertical direction of the lifter 100. Thus, one end of the expanding portions 110 may be disposed adjacent to the upper end 102 of the lifter 100, and another end of the expanding portions 110 may be disposed adjacent to the lower end 104 of the lifter 100.

In addition, the expanding portions 110 may be disposed separately from one another in a longitudinal direction of the lifter 100 or a lateral direction of the lifter 100. Thus, a portion of the expanding portions 110 may be disposed adjacent to a left end of the lifter 100 or to the left connector 200, and another portion of the expanding portions 110 may be disposed adjacent to a right end of the lifter 100 or to the right connector 300.

The expanding portions 110 may be expanded by injection of a fluid, and such an expansion of the expanding portions 110 may allow the lifter 100 to generate a tractive force along the longitudinal direction of the spinal column.

The blocking portions 120 may be disposed between an expanding portion and a neighboring expanding portion among the expanding portions 110.

The blocking portions 120 may be extended in the longitudinal direction of the spinal column or in the vertical direction of the lifter 100, and disposed separately from one another in the lateral direction of the lifter 100.

Although FIG. 1a illustrates three or four blocking portions being disposed in spaces between neighboring expanding portions among the expanding portions 110, the number of the blocking portions 120 is not limited to the example and various numbers of the blocking members 120 may be provided.

A fluid may not be injected into the blocking portions 120, and thus only the expanding portions 110 may be expanded when a fluid is injected into the lifter 100.

Due to the disposition of the expanding portions 110 and the blocking portions 120, a plurality of air columns extended upwards and downwards, for example, in a vertical direction, may be formed in the lifter 100.

In addition, through a space between neighboring blocking portions of the blocking portions 120, a fluid may be transferred from one neighboring expanding portion to another neighboring expanding portion of the expanding portions 110.

For example, according to an example embodiment, a fluid injection member 320 may be disposed in the right connector 300 of the lifting belt 10, and thus a fluid injected into the fluid injection member 320 may have directivity from a right side to a left side.

The expanding portions 110 and the blocking portions 120 may be provided in the lifter 100 as described hereinafter.

For example, the blocking portions 120 may be provided by stacking two fabric layers of a same size and bonding the layers at a certain location using a high frequency, and the expanding portions 110 may be provided in a space of the fabric layers that is not bonded by the high frequency.

However, the expanding portions 110 and the blocking portions 120 may not be provided in the lifter 100 through such a method described in the foregoing, and any methods that may form an air column extended in the vertical direction of the lifter 100 may be applicable.

In addition, the cut portions 130 may be disposed adjacent to the upper end 102 of the lifter 100, among the expanding portions 110.

For example, the cut portions 130 may be extended towards the lower end 104 from the upper end 102 of the lifter 100. Here, a cut width of each of the cut portions 130 may increase towards the lower end 104 from the upper end 102 of the lifter 100.

The cut portions 130 may be disposed separately from one another in the lateral direction of the lifter 100, and three or four expanding portions 110 may be disposed between the cut portions 130.

When a fluid is injected into the lifter 100, the expanding portions 110 may be expanded in the vertical direction of the lifter 100, and the cut width of the cut portions 130 may be decreased. Thus, a length of the upper end 102 of the lifter 100 may be shorter than a length of the lower end 104 of the lifter 100.

When the lifting belt 10 is worn on the user, the cut portions 130 may be used to prevent a compression by the lifter 100 from loosening in an upper portion of a waist of the user or an upper portion of an abdomen of the user.

In general, a circumference of the upper portion of the waist is smaller than a circumference of a lower portion of the waist due to a curve of the waist, and thus the upper end 102 of the lifter 100 may not be closely attached to the upper portion of the waist when the length of the upper end 102 of the lifter 100 is equal to the length of the lower end 104 of the lifter 100, and the tractive force generated by the lifter 100 may not be readily applied to the user. Thus, the length of the upper end 102 of the lifter 100 may need to be shorter than the length of the lower end 104 of the lifter 100.

The lifting belt 10 may include the cut portions 130 at the upper end 102 of the lifter 100, and thus the length of the upper end 102 of the lifter 100 may be shorter than the length of the lower end 104 of the lifter 100. However, examples are not limited to the foregoing, and any methods that may form the length of the upper end 102 of the lifter 100 to be shorter than the length of the lower end 104 of the lifter 100 may be applicable.

For example, the cut portions 130 may be provided at the upper end 102 of the lifter 100 with the cut portions 130 being shrunk and the upper end 102 of the lifter 100 being piped to form the length of the upper end 102 of the lifter 100 to be shorter than the length of the lower end 104 of the lifter 100.

In addition, referring to FIG. 1b, the lifter 100 includes at least one flap member 140.

The flap member 140 may be provided to cover an inner surface of the lifter 100.

For example, in a case that a plurality of flap members is provided as the flap member 140 to cover the inner surface of the lifter 100, the flap member 140 may include a first flap member 142 extended to a center of the lifter 100 from the upper end 102 of the lifter 100, and a second flap member 144 extended to the center of the lifter 100 from the lower end 104 of the lifter 100.

Alternatively, in a case that a single flap member is provided as the flap member 140 to cover the inner surface of the lifter 100, the flap member 140 may be extended towards the lower end 104 from the upper end 102 of the lifter 100, or extended towards the upper end 102 from the lower end 104 of the lifter 100.

Here, a total height of the flap member 140 may be shorter than the height of the lifter 100.

The total height of the flap member 140 may be, for example, a sum of respective heights of the first flap member 142 and the second flap member 144, or a total length of the single flap member 140. The height of the lifter 100 may indicate a height measured before a fluid is injected, or a height measured after a fluid is injected.

The total height of the flap member 140 may be desirably shorter than the height of the lifter 100 measured before a fluid is injected into the lifter 100, for example, a distance between the upper end 102 and the lower end 104 of the lifter 100

The flap member 140 may be provided to reduce inconvenience the user may experience due to unevenness of the expanding portions 110 when the user wears the lifting belt 10. For example, in a case that the total height of the flap member 140 is longer than the height of the lifter 100, the flap member 140 may overlap when the lifter 100 is expanded, and thus may cause inconvenience. Such an inconvenience may induce an unnecessary pressure or pain.

In addition, the flap member 140 may be formed of, for example, a suede material, and thus may increase a frictional force with the torso of the user.

The lifter 100 also includes an elastic member 150 configured to connect the upper end 102 and the lower end 104 of the lifter 100.

The elastic member 150 may be disposed inside the lifter 100, and extended towards the lower end 104 from the upper end 102 of the lifter 100.

For example, the elastic member 150 may be disposed in the expanding portions 110 and deformed by expansion of the expanding portions 110, and the expanding portions 110 may return to an original state by contraction of the elastic member 140.

The left connector 200 and the right connector 300 may be disposed on a left side and right side of the lifter 100, respectively.

The left connector 200 may be connected to the left side of the lifter 100 and the right connector 300 may be connected to the right side of the lifter 100, and the left connector 200 and the right connector 300 may be connected to each other through the central connector 400.

Here, the left connector 200 and the right connector 300 may be bilaterally symmetrical with each other relative to the lifter 100.

The central connector 400 may be attached to or detached from at least one of the left connector 200 and the right connector 300. Based on a location at which the central connector 400 is attached to or detached from the left connector 200 or the right connector 300, a length of the central portion 400 that is externally exposed may be adjusted.

Referring to FIG. 2a, in a case that the left connector 200 and the central connector 400 are provided in an integral type, a velcro (V) may be provided to an outer surface of the central connector 400 and an inner surface of the right connector 300, and the velcro V on the inner surface of the right connector 300 may be attached to the velcro V on the outer surface of the central connector 400 to connect the left connector 200 and the right connector 300. In such a case, a risk of loss of the central connector 400 may be reduced.

Alternatively, referring to FIG. 2b, in a case that the left connector 200 and the central connector 400 are provided in a separate type, a velcro (V) may be provided to the outer surface of the central connector 400 and respective inner surfaces of the left connector 200 and the right connector 300. Thus, the velcro V on the inner surface of the left connector 200 and the velcro V on the inner surface of the right connector 300 may be respectively attached to the velcro V on the outer surface of the central connector 400 to connect the left connector 200 and the right connector 300. In such a case, the length of the central connector 400 that is externally exposed may be adjusted identically for each of an end of the left connector 200 and an end of the right connector 300, and thus such a separate type may prevent the tractive force generated by the lifter 100 from being offset by the central connector 400.

In addition, the left connector 200 and the right connector 300 include a plurality of indication members.

The indication members include a first indication member 210 disposed on the outer surface of the left connector 200 and a second indication member 310 disposed on the outer surface of the right connector 300.

The first indication member 210 and the second indication member 310 may be disposed to be bilaterally symmetrical with each other.

Referring to FIG. 1c, in a state in which the left connector 200 and the right connector 300 are connected to each other, or the lifting belt 10 is worn on the user, the central connector 400 may be disposed between the first indication member 210 and the second indication member 310. Thus, by verifying a location of the first indication member 210, the second indication member 310, or the central connector 400, whether the lifting belt 10 is desirably worn may be verified.

In addition, by disposing the central connector 400 at a center of the abdomen, the lifting belt 10 may be desirably worn, and thus the tractive force generated by the lifter 100 may be effectively applied to the spinal column and also a waist tractive effect and an effect of supporting muscles around the waist may be obtained.

In addition, the left connector 200 or the right connector 300 includes the fluid injection member 320 to supply a fluid to the lifter 100.

Hereinafter, a case in which the fluid injection member 320 is disposed in the right connector 300 will be described as an example.

Referring to FIG. 3, a fluid injector A may be connected to the fluid injection member 320. The fluid injector A may inject a fluid, for example, air, into the fluid injection member 320.

The fluid injected into the fluid injection member 320 may expand the expanding portions 110 sequentially, starting from an expanding portion among the expanding portions 110 that is disposed adjacent to the right connector 300 to an expanding portion among the expanding portions 110 that is disposed adjacent to the left connector 200, or expand the expanding portions 110 simultaneously.

Referring to FIGS. 4a and 4b, a lower end 322 of the fluid injection member 320 may be provided in a circular shape or an oval shape.

Here, based on a shape of the lower end 322 of the fluid injection member 320, a degree of abrasion of the fabric layers forming the lifting belt 10 may change. For example, in a case that the fabric layers are severely abraded, a hole may be formed in a portion adjacent to the fluid injection member 320, and the fluid injected into the fluid injection member 320 may flow out through the hole.

As illustrated in FIG. 4b, in a case that the lower end 322 of the fluid injection member 320 is provided in an oval shape, at the lower end 322 of the fluid injection member 320, a major axis (MA) may be disposed parallel to the upper end 102 or the lower end 104 of the lifter 100, and thus a degree of flatness of the fabric layers may be greater compared to the case in which the lower end 322 of the fluid injection member 320 is provided in the circular shape. Thus, a pressure or a load to be applied to the fabric layers may be dispersed, and thus the degree of abrasion of the fabric layers may be reduced despite a long-term use of the lifting belt 10 and also durability of the fabric layers may increase.

Referring to FIGS. 5a through 5c, when a fluid is injected into the lifter 100, the expanding portions 110 may be expanded upwards and downwards, for example, in a vertical direction, and thus the tractive force may be generated along the longitudinal direction of the spinal column of the user. Here, leftward or rightward expansion of the expanding portions 110 may be restricted by the blocking portions 120 or the cut portions 130.

As described above, the expanding portions 110 may be expanded upwards and downwards to allow the spinal column to resist gravity, and thus the lifting belt 10 may stably lift a weight of an upper body of the user in a vertical direction and ease a backache or a back pain from which the user may suffer. In addition, air columns may be formed by the expanding portions 110, and thus the lifting belt 10 may be transformed to be elastic in response to a curve or a movement of the waist of the user and accordingly more stably support muscles around the waist.

Further, as described above, when the expanding portions 110 are expanded by the cut portions 130, the length of the upper end 102 of the lifter 100 may become shorter than the length of the lower end 104, and thus an edge of the upper end 102 and the lower end 104 of the lifter 100 may be prevented from being spread towards an outer side by the injection of a fluid and the lifter 100 may be closely attached to a body of the user to more effectively transfer the tractive force to the spinal column of the user.

As described above, according to example embodiments, a lifting belt may be used to protect or treat a disc by being applied to various users, for example, a lumber disc patient experiencing a surgery or recovering from the surgery, an acute or chronic strain patient, and a student preparing examination, a worker or an employee, and a driver who are sedentary for most of times and thus need to have correction of posture, and an athlete who needs rehabilitation.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

The invention claimed is:

1. A lifting belt comprising:
   a lifter configured to generate a tractive force along a longitudinal direction of a spinal column by expansion; and
   a left connector and a right connector respectively disposed on a left side and a right side of the lifter, and connectable to each other, wherein
   the lifter comprises a plurality of expanding portions adapted to be extended in the longitudinal direction of the spinal column and configured to be expanded by injection of a fluid,
   a plurality of blocking portions disposed in a vertical direction of the lifter, among the plurality of expanding portions, and configured for restricting leftward or rightward expansion of the plurality of expanding portions, and
   a plurality of cut portions disposed adjacent to an upper end of the lifter, among the plurality of expanding portions,
   a cut width of each of the plurality of cut portions increases towards a lower end of the lifter from the upper end of the lifter,
   wherein when the fluid is injected into the lifter, the plurality of expanding portions expand in the vertical direction of the lifter, parallel to the longitudinal direction of the spinal column, and the cut width of each of the plurality of cut portions is decreased by expansion of the plurality of expanding portions,
   wherein a length of the upper end of the lifter is shorter than a length of the lower end of the lifter.

2. The lifting belt of claim 1, wherein the lifter comprises:
   at least one flap member disposed in an inner surface of the lifter,
   wherein a total height of the at least one flap member is shorter than a height of the lifter.

3. The lifting belt of claim 1, wherein the lifter comprises:
   a plurality of flap members disposed in an inner surface of the lifter,
   wherein the plurality of flap members comprise:
   a first flap member extended to a center of the lifter from the upper end of the lifter; and
   a second flap member extended to the center of the lifter from the lower end of the lifter.

4. The lifting belt of claim 1, wherein the left connector or the right connector comprises:
   a fluid injection member configured to supply a fluid to the lifter,
   wherein a lower end of the fluid injection member is provided in an oval shape, and
   a major axis from the lower end of the fluid injection member is parallel to the upper end or the lower end of the lifter.

5. The lifting belt of claim 1, wherein the lifter comprises:
   an elastic member disposed in each of the plurality of expanding portions and configured to connect the upper end of the lifter and the lower end of the lifter,
   wherein the elastic member is configured to be deformed by expansion of the plurality of expanding portions, and the plurality of expanding portions is adapted to return to an original state by contraction of the elastic member.

6. The lifting belt of claim 1, wherein the left connector and the right connector are bilaterally symmetrical with each other from the lifter,
   the lifting belt further comprising:
   a central connector attachable to or detachable from at least one of the left connector and the right connector.

7. The lifting belt of claim 6
   wherein the left connector and the right connector comprise:
   a plurality of indication members,
   wherein the plurality of indication members comprise:
   a first indication member disposed on an outer surface of the left connector; and
   a second indication member disposed on an outer surface of the right connector,
   wherein the central connector is disposed between the first indication member and the second indication member.

* * * * *